United States Patent [19]
Marzluff et al.

[11] Patent Number: 5,429,143
[45] Date of Patent: Jul. 4, 1995

[54] DEVICE AND METHOD FOR DETERMINING HOLE INTEGRITY IN SURGICAL APPLICATIONS

[76] Inventors: Joseph Marzluff, 131 Riverland Dr., Charleston, S.C. 29412; Jeffrey T. Root, 6231 Thom Rd., Graham, N.C. 27253

[21] Appl. No.: 155,485

[22] Filed: Nov. 22, 1993

[51] Int. Cl.6 ............................................. A61B 19/00
[52] U.S. Cl. .................................... 128/897; 128/774; 73/40
[58] Field of Search .............. 128/897, 748, 673, 749, 128/774; 604/48; 606/53; 73/37, 40

[56] References Cited

U.S. PATENT DOCUMENTS

| | | | |
|---|---|---|---|
| 4,739,769 | 4/1988 | Matthews et al. | 128/748 |
| 4,976,267 | 12/1990 | Jeffcott et al. | 128/774 |
| 5,032,111 | 7/1991 | Morris et al. | 604/48 |
| 5,303,718 | 4/1994 | Krajicek | 128/897 |
| 5,315,861 | 5/1994 | Egan et al. | 73/37 |
| 5,343,863 | 9/1994 | Wiener et al. | 128/660.01 |
| 5,348,009 | 9/1994 | Ohtomo et al. | 128/660.01 |
| 5,368,044 | 11/1994 | Cain et al. | 128/774 |

Primary Examiner—Lee S. Cohen
Assistant Examiner—Brian L. Casler
Attorney, Agent, or Firm—B. Craig Killough

[57] ABSTRACT

Liquid material is directed under pressure into a hole, such as a hole formed in a bone. The vessel from which the liquid is directed, such as a syringe or squeeze bulb tube, provides a seal at the point of contact between the vessel and the hole to maintain a closed system. After the liquid is directed into the hole, a continued drop in liquid volume within the vessel is accompanied by a rapid drop in air pressure, which is measured by a gauge, indicating a deficit in the structural integrity of the hole.

11 Claims, 2 Drawing Sheets

DEVICE AND METHOD FOR DETERMINING HOLE INTEGRITY IN SURGICAL APPLICATIONS

FIELD OF THE INVENTION

This invention relates generally to surgical devices, and is particularly directed to a device which aids in determining the integrity of holes formed in bones for the subsequent insertion of screws or other fasteners or devices, and also is directed to a method of using the device.

BACKGROUND OF THE INVENTION

Surgeons frequently form holes in bones. Such holes are, in many instances, subsequently tapped to allow the insertion of metal or plastic screws. Screws are used to fasten devices which repair degenerative, congenital or trauma related defects.

Defects in the hole resulting from drilling or tapping of the hole, or from insertion of the screw commonly result. Screw threads or screw tips protrude from the bone due to, for example, a defect in cortical integrity from improper placement or preparation of the hole.

A protrusion of the threads from the hole, or a tip of the screw protruding from the hole, or other defects in the hole, may result in the screw failing to hold properly. Further such defects may cause complications to the patient resulting from the surgery. For example, if a hole is drilled and tapped for the placement of pedicle screws during lumbosacral stabilization, cauda equina or nerve root injury may result. Neurological deficit to the patient may therefore occur due to the incorrect placement or tapping of the pedicle hole.

Techniques which are commonly used for determination of screw hole placement include radiographs, fluoroscopy or visual inspection of the wall. These means are not reliable.

Palpation of the prepared screw hole has also been employed. One method of palpating the hole involves the use of a wire probe by which the surgeon feels the circumference of the hole for any area which that is not encompassed with bone. This method is inaccurate, and can actually cause neurological deficit from contact with the probe. Where a tapped hole is present, the reliability of palpation further diminishes.

Devices are available which detect the differences in conductivity between bone and body tissue. If the bone is not providing complete "insulation", then an indication is provided that there is a defect in the integrity of the screw hole. This method is probably more accurate than the methods discussed above, but is relatively expensive, and does not give an indication of the size or location of the defect.

A very simple test for checking screw hole integrity involves placing water within the screw hole. If there is a defect in the screw hole, the water will run out. Through the use of water containing a dye, a better indication of the location of the screw hole is indicated. This method can be used in most applications, but gives little indication of the size of the defect.

SUMMARY OF THE INVENTION

The present invention comprises a vessel having a liquid material in a portion thereof, and air in a remaining portion. The air pressurized is increased by reducing the volume of the vessel, forcing the liquid, which may be saline solution, through an orifice located in the vessel. The orifice is inserted into the hole previously formed, with the contact between the orifice and the screw hole sealed, such as by a gasket, to prevent pressurized water from escaping from the hole.

The decreased volume of the vessel is maintained for several seconds. If the water seeps out of the hole, such as through a defect in the hole, the remaining liquid material will exit the vessel through the orifice, and the liquid volume within the vessel and the air pressure within the vessel will drop. The vessel may be attached to a pressure gauge, which measures any drop in air pressure. If the liquid volume does not continue to drop after the liquid is forced into the hole, there will either be no air pressure drop, or a slow drop in pressure, indicating the presence of structural integrity of the hole. If there is a defect in the hole, the rate of the liquid volume drop and/or air pressure drop within the vessel will give an indication as to the degree of the defect.

DESCRIPTION OF THE DRAWINGS

FIG. 3 is essentially identical to FIG. 2, excepting that FIG. 3 demonstrates a defective hole.

DETAILED DESCRIPTION OF THE PREFERRED EMBODIMENT

Figure 1:
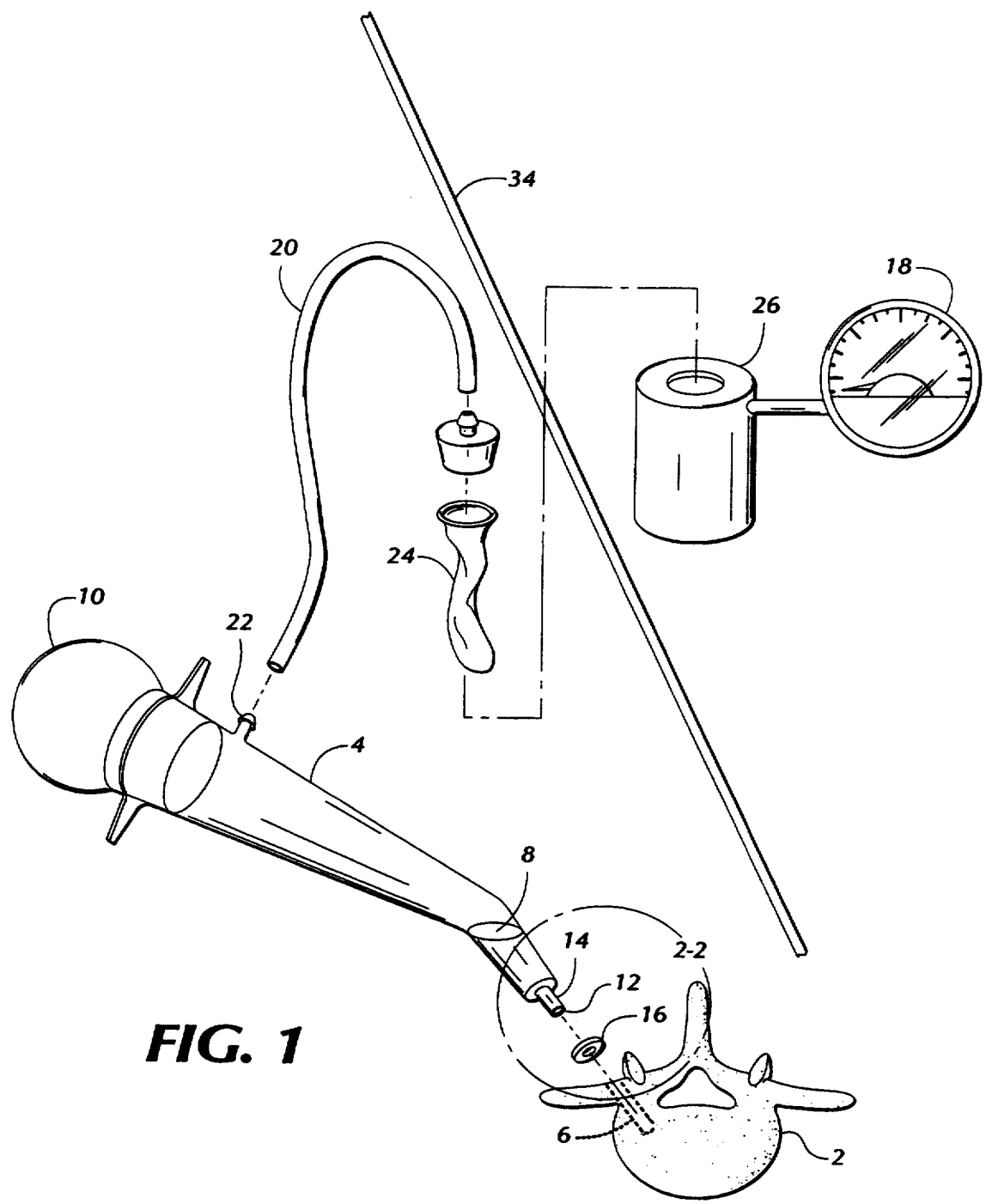
FIG. 1 is an exploded view of the device for determining hole integrity.

Referring to the drawing figures, FIG. 1 shows a spine 2 having a hole 6 drilled therein. A vessel 4 containing a liquid 8, which may be saline solution, is used to force the liquid into the hole. The pressure applying means or vessel, as shown in this embodiment, is a squeeze bulb tube.

Air is present within an upper portion of the squeeze bulb tube, while a liquid, such as saline solution, is present in the lower portion of the squeeze bulb tube. The vessel, or squeeze bulb tube, has a means 10 for reducing the volume of the vessel, so as to use air present in the tube to force the saline solution from the squeeze bulb tube, through the orifice 12 of the nipple 14 of the squeeze bulb tube, and into the hole 6. A gasket 16 is used to prevent liquid from flowing out of the hole through the top opening of the hole.

The system depicted in FIG. 1 is closed with regard to pressure drops and increases, so that a pressure gauge 18 may be connected to the vessel or squeeze bulb tube to measure increases and drops in pressure. Flexible tubing 20 is attached to a nipple 22 extending from the squeeze bulb tube. The nipple is present on the squeeze bulb tube above the level of the liquid within the tube so that as the squeeze bulb tube is depressed, air is forced into the tube. A diaphragm which is non-porous and air tight, is affixed to the opposite end of the flexible tubing. As the volume of the vessel is reduced, such as by depressing the squeeze bulb, the liquid is forced from the tube through orifice 12, while air is forced through the orifice of the upper nipple 22, expanding the diaphragm.

The diaphragm is contained in a diaphragm canister 26, which is air tight. As the diaphragm expands, it in turn forces air from the diaphragm canister through the tubing which is connected to pressure gauge 18. As air is forced from the diaphragm canister, the pressure increase through the tubing is detected by the pressure gauge.

Figure 2:
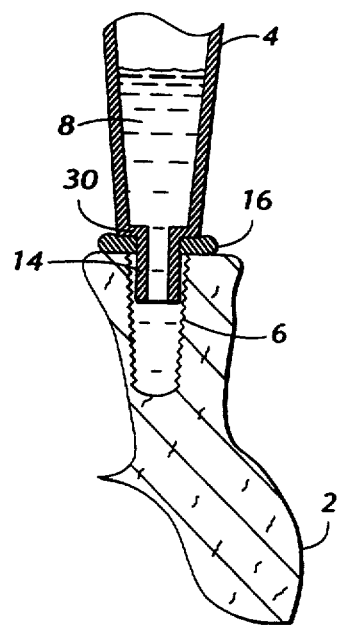
FIG. 2 is a sectioned view taken essentially along line 2—2 of FIG. 1.
Figure 3:
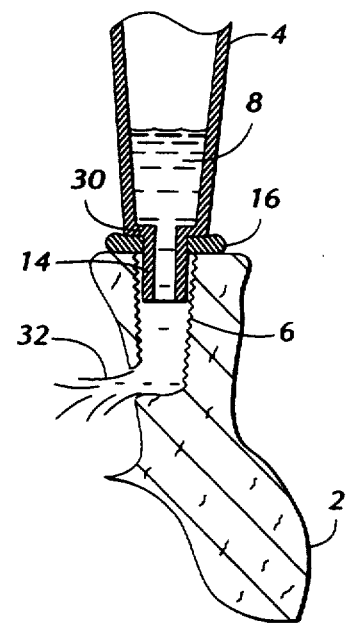
FIG. 3 is a sectioned view taken essentially along line 2—2 of FIG. 1.
Figure 4:
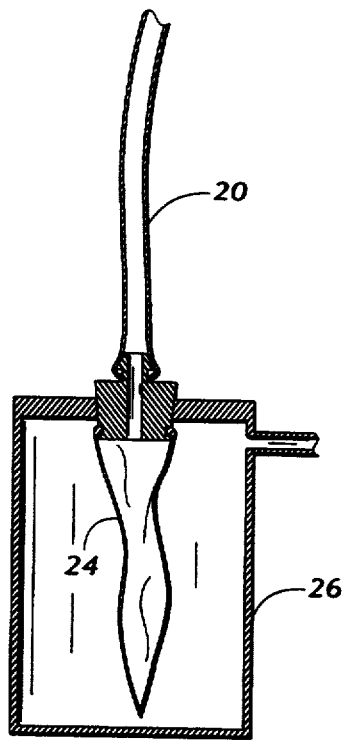
FIG. 4 is a side, sectioned view of the diaphragm canister.
Figure 5:
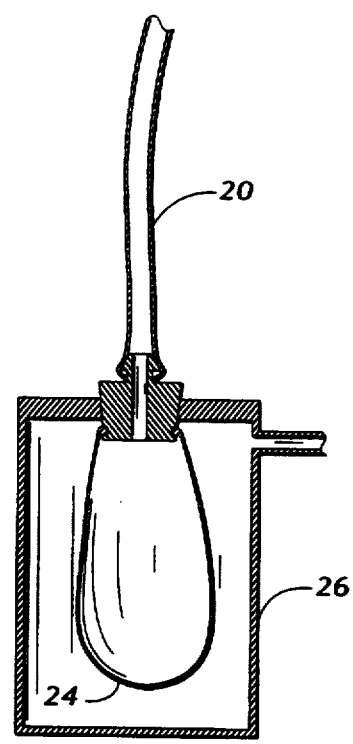
FIG. 5 is a side, sectioned view of the diaphragm canister of FIG. 4, with the diaphragm expanded.

In use, the nipple of the vessel is inserted into the hole in the bone as shown in FIG. 2 and FIG. 3. The gasket surrounds the nipple, and seats on the shoulder 30 of the vessel adjacent to the nipple, and also seats on the surface of the bone. The gasket material should be a relatively soft material which will seal the vessel against the surface of the bone to prevent the solution from escaping from around the gasket. A gasket formed of soft silicone, for example, will adequately perform this function.

The effective volume of the vessel is then reduced. In the preferred embodiment a squeeze bulb 10 is used to perform this function. Manually squeezing the squeeze bulb reduces the volume of the vessel, thereby increasing the air pressure within the vessel. This increase in air pressure forces water into the hole as shown in FIG. 2. If the structural integrity of the hole is intact as shown in FIG. 2, air is transferred into the diaphragm, causing the diaphragm to expand, reducing the remaining volume of diaphragm canister, and causing an increase in pressure which is measured by a pressure gauge.

When the squeeze bulb is squeezed, it is held in the squeeze position for several seconds. In the preferred embodiment, holding the squeeze bulb for ten seconds or less will provide a sufficient indication of the structural integrity of the hole. If the hole is structurally intact, and not defective, as shown in the hole of FIG. 2, the pressure shown on the pressure gauge will not drop, or will drop slowly, assuming that the device is properly seated by means of the gasket against the hole. If no pressure drop is noted on the pressure gauge while the squeeze bulb is depressed, or the pressure drop is slow, then a hole having the desired structural integrity is present.

FIG. 3 demonstrates a hole which has been improperly drilled and is defective, so as to have a break on the lower end of the hole. In this case, when the squeeze bulb is depressed, the solution will be forced into the hole. Momentarily, the pressure gauge will give an increased reading as air is forced into the diaphragm. However, as water escapes through the defect 32, the volume of liquid and the air pressure in the system decreases, and the pressure gauge will drop relatively rapidly, indicating a defective hole.

The diaphragm canister 26 allows relatively inexpensive sterile elements to be separated from the more expensive elements of the device. In this way, the non-sterile elements may be reused, while the sterile elements may be discarded. Line 34 of FIG. 1 demonstrates the separation between the sterile elements and the non-sterile elements.

Other means could be provided for applying pressure. Syringe-type devices or other similar means which will reduce the volume of the vessel as desired to increase air pressure may be used. However, the squeeze bulb tube allows the volume to be quickly reduced to an approximately uniform volume for each repetition with a simple squeeze of the squeeze bulb.

Squeeze bulb tubes in the configuration of the preferred embodiment are readily available in sterile packaging. The squeeze tube may also be used as an irrigator during surgery.

A relatively rapid drop in the pressure gauge reading indicates a hole having a defect through which the saline solution or other liquid is escaping. Through empirical observation, a determination as to the size of the defect may be made by the rate of the drop in pressure. In many cases, by observing the travel of the saline, the location of the defect can be determined.

A drop in the remaining volume of liquid within the squeeze tube or other pressure applying means after the hole is injected with liquid also indicates a defect in the structural integrity of the hole. Lines or other series of marks placed on the vessel allow the user to determine if the level is static, indicating structural integrity, or to determine a decrease in volume of the liquid material, indicating a defect.

What is claimed is:

1. A device for detecting defects in prepared holes in bones, comprising:
   a. a pressure applying means having a liquid material contained therein, and having an orifice therein through which said liquid material is transferred, and having a nipple which extends from said pressure applying means, wherein said orifice is in said nipple, and wherein said nipple is adapted to extend into a hole in a bone; and
   b. a pressure gauge which communicates with said pressure applying means to detect changes in air pressure within said pressure applying means after said liquid is transferred into said hole in said bone.

2. A device for detecting defects in prepared holes in bones as described in claim 1, further comprising a canister which is connected to said pressure applying means, and a diaphragm which is present within said canister, and wherein said pressure gauge is connected to said canister.

3. A device for detecting defects in prepared holes in bones as described in claim 2, wherein said pressure applying means further comprises a means for selectively reducing a volume of said pressure applying means to cause said liquid material to be transferred from said pressure applying means through said orifice.

4. A device for detecting defects in prepared holes in bones as described in claim 1, wherein said pressure applying means further comprises a means for selectively reducing a volume of said pressure applying means to cause said liquid material to be transferred from said pressure applying means through said orifice.

5. A device for detecting defects in prepared holes in bones as described in claim 1, wherein said pressure applying means further comprises a gasket which surrounds said nipple, and wherein said gasket is adapted to contact a surface of said bone.

6. A device for detecting defects in prepared holes in bones as described in claim 5, further comprising a canister which is connected to said pressure applying means, and a diaphragm which is present within said canister, and wherein said pressure gauge is connected to said canister.

7. A device for detecting defects in prepared holes in bones as described in claim 6, wherein said pressure applying means further comprises a means for selectively reducing a volume of said pressure applying means to cause said liquid material to be transferred from said pressure applying means through said orifice.

8. A device for detecting defects in prepared holes in bones as described in claim 5, wherein said pressure applying means further comprises a means for selectively reducing a volume of said pressure applying means to cause said liquid material to be transferred from said pressure applying means through said orifice.

9. A method for detecting defects in prepared holes in bones, comprising the steps of:
   a. providing a pressure applying means;
   b. placing a liquid material within said pressure applying means;
   c. transferring said liquid material into a hole in a bone using said pressure applying means;
   d. reading a pressure gauge which is connected to said pressure applying means; and
   e. determining a rate of drop in pressure of air contained in said pressure applying means to determine if a defect is present in said hole in said bone.

10. A device for detecting defects in prepared holes in bones, comprising a pressure applying means which transfers a liquid material contained within said pressure applying means into a hole in a bone by forcing air contained within said pressure applying means against said liquid material, an orifice in said pressure applying means through which said liquid material exits said pressure applying means, wherein said pressure applying means further comprises a means for selectively reducing an internal volume of said pressure applying means to increase air pressure within said pressure applying means to force said liquid from said pressure applying means through said orifice, and wherein said pressure applying means further comprises a nipple which extends from said pressure applying means and is adapted to extend into said hole in said bone, wherein said orifice is contained in said nipple, and further comprises a gasket which surrounds said nipple and is adapted to contact a surface of said bone.

11. A method for detecting defects in prepared holes in bones, comprising the steps of:
   a. providing a pressure applying means;
   b. placing a liquid material within said pressure applying means;
   c. using said pressure applying means to transfer said liquid material from said pressure applying means into a hole in a bone until said hole is completely filled with liquid; and
   d. determining if a remaining portion of liquid within said pressure applying means remains static or continues to drop after said liquid is transferred into said hole and said hole is filled with liquid.

* * * * *